(12) United States Patent
Lascola et al.

(10) Patent No.: US 9,007,576 B2
(45) Date of Patent: Apr. 14, 2015

(54) SURFACE ENHANCED RAMAN SCATTERING SPECTROSCOPIC WAVEGUIDE

(75) Inventors: Robert J. Lascola, N. Augusta, SC (US); Christopher S. McWhorter, Evans, GA (US); Simona H. Murph, N. Augusta, SC (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 105 days.

(21) Appl. No.: 13/136,888

(22) Filed: Aug. 12, 2011

(65) Prior Publication Data
US 2013/0038869 A1 Feb. 14, 2013

(51) Int. Cl.
- G01J 3/44 (2006.01)
- G01N 21/65 (2006.01)
- B82Y 30/00 (2011.01)
- B82Y 20/00 (2011.01)

(52) U.S. Cl.
CPC .............. *G01N 21/658* (2013.01); *B82Y 30/00* (2013.01); *B82Y 20/00* (2013.01)

(58) Field of Classification Search
USPC ...................................... 356/301, 72–73, 246
See application file for complete search history.

(56) References Cited

U.S. PATENT DOCUMENTS

| | | | |
|---|---|---|---|
| 7,151,599 B2 | 12/2006 | Islam | |
| 7,295,723 B2 * | 11/2007 | Hyde | ............................... 385/12 |
| 7,428,046 B2 | 9/2008 | Wang | |
| 7,576,854 B2 | 8/2009 | Wang | |
| 7,588,827 B2 | 9/2009 | Nie | |
| 7,639,356 B2 | 12/2009 | Prokes | |
| 7,656,525 B2 | 2/2010 | Zhao | |
| 7,713,849 B2 | 5/2010 | Habib | |
| 7,727,776 B2 | 6/2010 | Zhou | |
| 7,764,374 B2 | 7/2010 | Hubter | |
| 7,776,425 B2 | 8/2010 | Kalkan | |
| 7,867,770 B2 | 1/2011 | Permasiri | |
| 7,929,133 B2 | 4/2011 | Wang | |
| 7,931,866 B2 | 4/2011 | Sun | |
| 2009/0263912 A1 | 10/2009 | Yang et al. | |

(Continued)

FOREIGN PATENT DOCUMENTS

| | | |
|---|---|---|
| WO | WO2008033763 | 3/2008 |
| WO | WO2011002988 | 3/2011 |

OTHER PUBLICATIONS

Pearman, et al., "Quantitative Measurements of CO2 and Ch4 using a multiplass Raman capillary cell", Sep. 1, 2008, Optical Society of America, vol. 47, No. 25, Applied Optics, pp. 4627-4362.

(Continued)

*Primary Examiner* — Abdullahi Nur
(74) *Attorney, Agent, or Firm* — J. Bennett Mullinax, LLC

(57) ABSTRACT

A waveguide for use with surface-enhanced Raman spectroscopy is provided that includes a base structure with an inner surface that defines a cavity and that has an axis. Multiple molecules of an analyte are capable of being located within the cavity at the same time. A base layer is located on the inner surface of the base structure. The base layer extends in an axial direction along an axial length of an excitation section. Nanoparticles are carried by the base layer and may be uniformly distributed along the entire axial length of the excitation section. A flow cell for introducing analyte and excitation light into the waveguide and a method of applying nanoparticles may also be provided.

19 Claims, 6 Drawing Sheets

(56) References Cited

U.S. PATENT DOCUMENTS

2010/0267013 A1* 10/2010 Su et al. .................... 435/6
2011/0036994 A1   2/2011 Frayling
2012/0242987 A1*  9/2012 Liu et al. ................... 356/301

OTHER PUBLICATIONS

Pearmn, et al., "Multipass Capillary Cell for Enhanced Raman Measurements of Gases"; Applied Spectroscopy, vol. 62, No. 3, 2008, pp. 285-289.

Kudelski, et al., "Flucutuations of surface-enhanced raman spectra of CO absorbed on gold substrates", Chemical Physics Letter 283 (2004) pp. 76-79.

Rae, et al.; "Surface enhanced Raman Spectroscopy (SERS) sensors for gas analysis"; The Royal Soeciety of Chemistry 2010, Analyst, 2010, 135 1365-1369.

Shi, et al.; Inner Wall Coated Hollow Core Waveguide Sensor Based on Double Substrate surface Enhanced Raman Sattering: 2008 American Institute of Physics: 93, 153101-1-3.

* cited by examiner

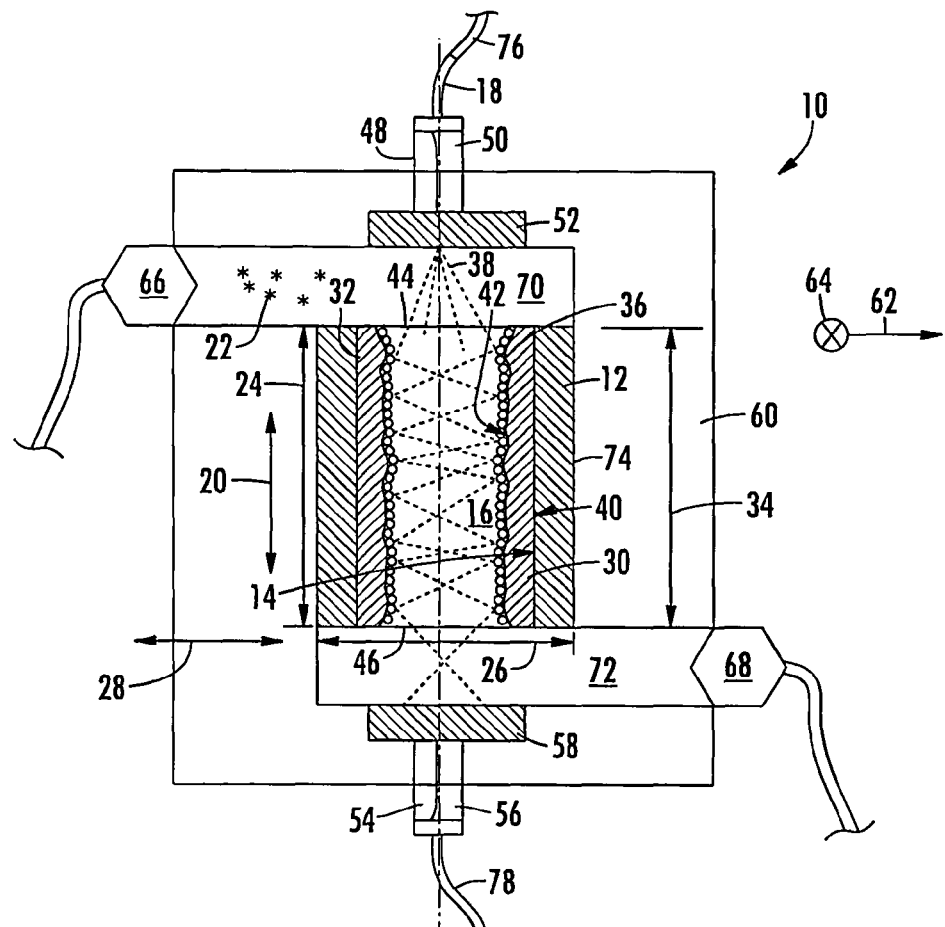
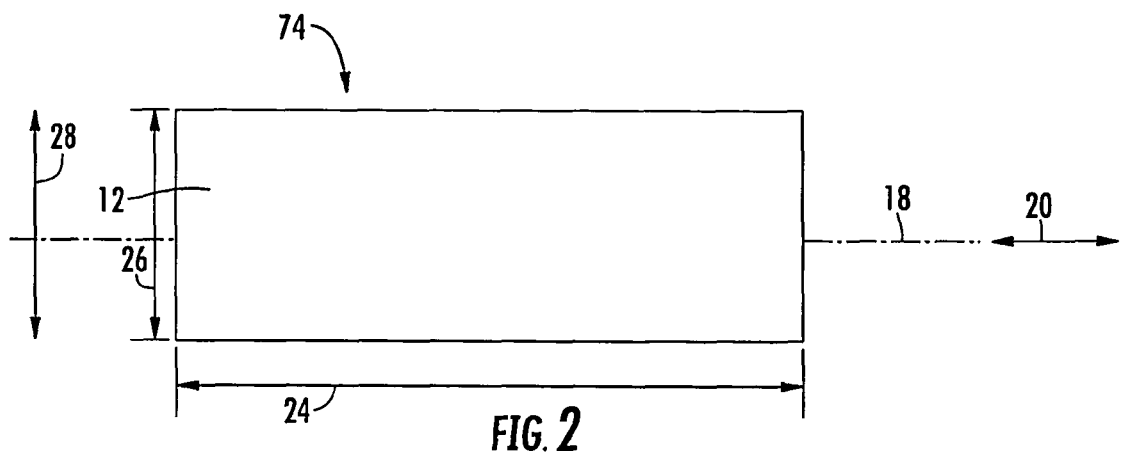
FIG. 1
FIG. 2

1, 4-butanedithiol

HS(CH$_2$)$_4$SH 1, 9-nonanedithiol

HS(CH$_2$)$_9$SH cysteamine

H$_2$NCH$_2$CH$_2$SH

SURFACE ENHANCED RAMAN SCATTERING SPECTROSCOPIC WAVEGUIDE

STATEMENT AS TO RIGHTS TO INVENTIONS MADE UNDER FEDERALLY SPONSORED RESEARCH AND DEVELOPMENT

This invention was made with Government support under Contract No. DE-AC09-08SR22470 awarded by the United States Department of Energy. The Government has certain rights in the invention.

FIELD OF THE INVENTION

The present invention relates generally to a waveguide for use with surface enhanced Raman spectroscopy, a flow cell for introducing a sample into the waveguide, and a method of applying nanoparticles. More particularly, the present application involves introduction of the excitation light in an axial direction through the capillary/waveguide in which the capillary/waveguide may have nanoparticles carried by a base layer.

BACKGROUND

Raman spectroscopy is a known technique of identifying the molecular composition of gases and liquids. Light, such as laser light, is directed onto the substance in question and interacts with the electron cloud of the molecules of the substance to an extent determined by the molecular polarization potential of the molecule. The oscillating electrons emit light primarily at the frequency of the incident laser ("Rayleigh scattering"). A small fraction of the light emitted occurs at different frequencies ("Raman scattering"), which correspond to vibrational energies of the molecules in the substance. The shift in the emitted photon's frequency away from the excitation frequency is known as the Raman shift. The observed pattern of Raman shift frequencies is a spectral fingerprint that allows one to identify the molecular components of the substance. This identification technique may be carried out without the need for an electrical current, so that concerns over flammability are reduced. Further, this identification technique may be less prone to nonspecific responses, may allow for the identification of gases such as hydrogen and oxygen which may not be detectable by other optical analysis methods such as infrared absorption spectroscopy, and may be dependable in challenging environments such as those that feature high humidity. However, the intensity of the Raman scattering is weak, and thus larger quantities of the analyte must be present to be detected, compared to other techniques.

Surface enhanced Raman spectroscopy (SERS) is a technique that is used to enhance the relatively weak Raman effect. A substrate that includes one or several noble metals, but typically gold and/or silver, may be used to carry out the SERS process. The gold or silver may have a roughness or patterned feature on the scale of 100 nm. Here, surface plasmons of the gold or silver are excited by the excitation light to result in an increased electrical field and a stronger Raman signal. The frequencies at which the electric field is enhanced are determined by the size of the features on the gold or silver. Selecting feature sizes so that the plasmon frequencies that are resonant with laser and Raman scattering frequencies will increase the efficiency of the Raman process. The increased effect may be achieved for molecules in proximity to particular surfaces where locally intense electric fields are present due to the excitement of plasmons.

Other techniques have been proposed in order to attempt to increase the sensitivity of the Raman measurement through the SERS effect. One such design employs a double substrate approach in which the analyte is coupled to nanoparticles that are suspended in a solution, and then the nanoparticles are coupled to a surface through non-specific interactions with a surface coating. This design is limited to use with a liquid analyte as nanoparticles placed into a gas analyte matrix would not be feasible. Further, the reliance on the random configuration of the nanoparticles and the analyte does not lead to efficient enhancement.

Another technique for SERS enhancement makes use of a SERS-active surface on the inside of a glass vial. The laser that generates the excitation light is directed in a radial direction into the glass vial and thus enters the side of the glass vial. This technique interrogates a single point on the SERS surface and does not support sampling of a large surface area. Although attempts to increase the sensitivity of a SERS process have been made, there remains room for variation and improvement in the art.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended Figs. in which:

FIG. 1 is a partial cross-sectional view of a waveguide and flow cell in accordance with one exemplary embodiment.

FIG. 2 is a side view of a capillary/waveguide in accordance with one exemplary embodiment.

Figure 3:
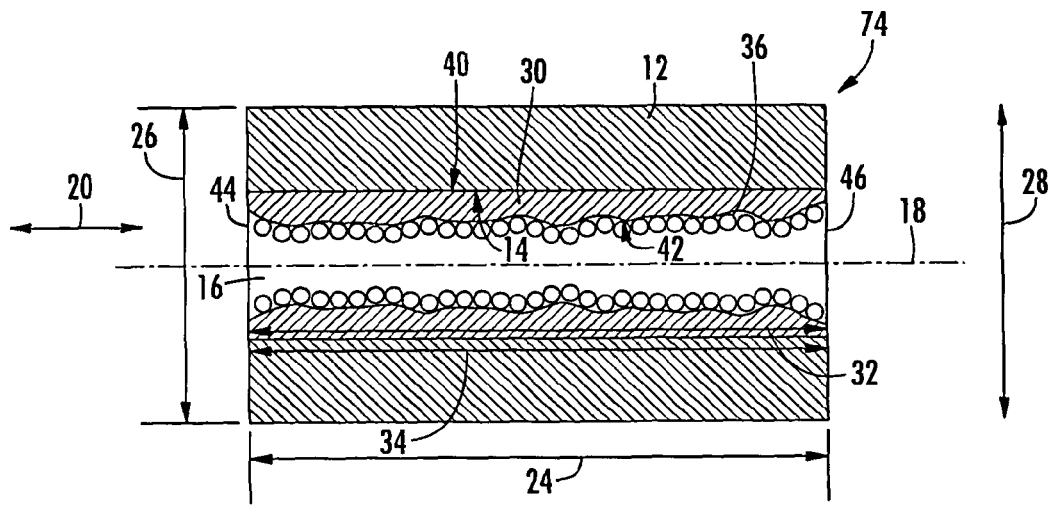
FIG. 3 is a cross-sectional view of the capillary/waveguide of FIG. 2.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for a waveguide 74 that can be used in a surface-enhanced Raman spectroscopy (SERS) process for identification of the composition of an analyte 22 such as a gas. The waveguide 74 may include a base structure 12 and a base layer 30 carried by the base structure 12. A nanoparticle array 36 may be carried by the base layer 30 such that the analyte 22 may be located adjacent to the nanoparticle array 36 on the base structure 12. The nanoparticle array 36 may function to enhance sensitivity of the identification process when a laser 48 is used to excite the interior of the waveguide 74 and a sensor 50 collects the scattered light for analyte 22 identification. The waveguide 74 may be arranged in a flow cell 10 so that the excitation light 38 is directed in an axial direction 20 to effect a very wide surface area that may lead to increased sensitivity of the measurement.

FIG. 1 discloses a flow cell 10 in accordance with one exemplary embodiment of the present invention. The flow cell 10 may include a spring loaded chuck 60 that has an inlet port 66 and an outlet port 68. An analyte 22 can be transferred through a hose or other line into inlet port 66 and then into an internal passageway 70 of the spring loaded chuck 60. The analyte 22 may next travel into the waveguide 74 and through this structure exiting at an internal passageway 72. An outlet port 68 is in communication with internal passageway 72 so that the analyte 22 can exit therethrough and out of the flow cell 10. With such an arrangement, analyte 22 may be continuously channeled through the flow cell 10 and reintroduced back into the system it came from, or vented to the atmosphere, so that continual analysis of the system can be accomplished. However, it is to be understood that other arrangements exist in which the analyte 22 is not transferred out of the flow cell 10 but is instead maintained within the flow cell 10 and analyzed.

Figure 4:
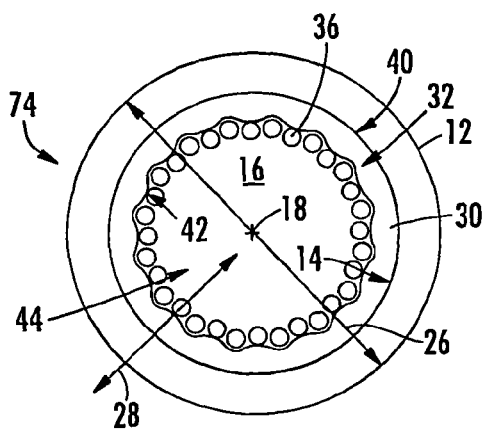
FIG. 4 is a front view of the capillary/waveguide of FIG. 2.

The capillary/waveguide 74 portion of the flow cell 10 may include a base structure 12. The capillary/waveguide 74 is shown with reference to FIGS. 2-4. The base structure 12 may be a tube that is open on both ends and that defines a cavity 16. The cavity 16 may be a through cavity in that it may extend from an inlet 44 on one end of the base structure 12 to an outlet 46 on an opposite end of the base structure 12 so that the base structure 12 is open on both ends with the cavity 16 extending completely therethrough. An axis 18 may extend through the center of the cavity 16 such that the wall portion of the base structure 12 is symmetrical about the axis 18. The base structure 12 may be arranged so that it is longer in an axial direction 20 than in a radial direction 28. In this regard, the axial length 24 of the base structure 12 can be longer than the radial length 26 of the base structure 12. The radial length 26 may be the outer diameter of the base structure 12 when the base structure 12 is configured as a tube. The base structure 12 may be made of a variety of material. In accordance with one embodiment, the base structure 12 is made of glass.

The capillary/waveguide 74 may be provided with a base layer 30 to support waveguide-like propagation of light in the axial direction 20 of the base layer 30. As disclosed, a base layer 30 can be carried by the base structure 12 and may engage an inner surface 14 of the base structure 12. In this regard, an outer surface 40 of the base layer 30 engages the inner surface 14 of the base structure 12. The base layer 30 may be made of gold in one embodiment. In accordance with another exemplary embodiment, the base layer 30 may be made of silver. The base layer 30 may be a thin layer of bulk gold that is bonded to the inner surface 14 in accordance with one embodiment. By making the base layer 30 sufficiently thick, it may allow base structure 12 to function as a waveguide during SERS analysis.

An excitation section 32 may be denoted as being the portions of the capillary/waveguide 74 that include the base layer 30 that are used to achieve the enhanced Raman effect. The excitation section 32 may be the entire axial length of the base layer 30. The axial length 34 may be greater than the radial length of the excitation section 32. In some instances, the base layer 30 extends along the entire axial length 24 of the base structure 12 and the axial length 34 of the excitation section 32 is the same as axial length 24. In other embodiments, the base layer 30 may not extend the entire axial length 24 and thus the axial length 34 of the excitation section 32 may be less than axial length 34. The excitation section 32 may include a nanoparticle array 36 when such nanoparticles 36 are present within the flow cell 10, and thus the nanoparticles 36 may act to form the excitation section 32.

The width or diameter of the excitation section 32 can be less than the axial length 34. The width or diameter of the cavity 16 can be less than the axial length of the cavity 16. Also, the width or diameter of the base structure 12 can be less than the axial length 24. Further, the width or diameter of the base surface 30 can be less than the axial length of the base surface 30, and the width or diameter of the nanoparticles 36 can be less than the axial length of the nanoparticles 36.

The flow cell 10 may also include a nanoparticle array 36 that is carried by the base layer 30. The nanoparticle array 36 may be bonded to an inner surface 42 of the base layer 30. The nanoparticle array 36 may be a series of nanoparticles that are arranged in a particular direction or that are arranged in no particular direction. As such, it is to be understood that the term "array" as used herein is broad enough to include randomly dispersed and/or non-randomly dispersed nanoparticles. It is therefore the case that the term "nanoparticle array" is broad enough to be simply "nanoparticles." The term nanoparticle array may be used when talking about the entire amount of nanoparticles present simply as a term of convenience. As such, it is to be understood that the terms nanoparticles and nanoparticle array are interchangeable with one another.

The nanoparticles 36 may be 25-200 nanometers in size in accordance with various exemplary embodiments and may be made of the same material as the base layer 30, or may be made of a different material than the base layer 30. The nanoparticles 36 may be variously shaped. For example, the nanoparticles 36 can be spherical or cylindrical. Further, the nanoparticles 36 may all be made of the same material in certain arrangements or may be made of different materials from one another in other embodiments.

The nanoparticles 36 can be uniformly distributed on the base layer 30 such that the nanoparticles 36 are uniformly distributed along the entire axial length 34 of the excitation section 32. With respect to the degree of uniformity required, it is noted that the exact same amount of nanoparticles 36 need not be present at every portion along the axial length 34. Regarding quantity of nanoparticles 36, as defined by either number or weight of nanoparticles 36, all portions of the axial length 34 may have an amount of nanoparticles 36 that are up to 1%, up to 3%, up to 5%, up to 10%, up to 15%, up to 20%, or up to 25% the same as one another. For example, an upper half of the axial length 34 of the excitation section 32 and a lower half of the axial length 34 of the excitation section 32 may have amounts of nanoparticles 36 that are up to 25% the same as one another. The nanoparticles 36 can be uniformly distributed so that when the excitation section 32 is broken up into 10 different sections in the axial direction 20, all of the ten sections include the same quantity of nanoparticles 36 as one another within a deviation of no more than up to 25%. There can be a significant amount of inner surface 42 exposed and not covered by the nanoparticles 36 yet the nanoparticles 36 can still be uniformly distributed along the axial length.

The uniformity of the nanoparticles 36 along the excitation section 32 may also be described with respect to their application on the inner surface 42 of the base layer 30. The nanoparticles 36 may be located 360° about axis 18 in the radial direction 28 on the inner surface 42 and along the entire axial length 34 such that there are no noticeable gaps or pockets of missing nanoparticles 36 along these areas. Alternatively, a smaller number/size of gaps of nanoparticles 36 can be present along the entire inner surface. The nanoparticles 36 may be uniformly applied such that the resulting surface roughness is consistent at the excitation section 32 along the entire axial length 34.

The nanoparticles 36 may be distributed along the entire axial length of the base layer 30, and in turn the base layer 30 may be located along the entire axial length 24 of the base structure 12 such that the nanoparticles 36 and base layer 30 extend along the entire base structure 12. When the base structure 12 is a tube, the base layer 30 may coat the entire inner surface 14 of the tube, and the nanoparticles 36 may coat the entire inner surface 42 of the base layer 30 such that the cavity 16 is closest to and defined by the nanoparticles 36. In other arrangements, the nanoparticles 36 are present on the inner surface 42 but do not completely cover the inner surface 42 such that portions of the inner surface 42 of the base layer 30 are visible when viewing same from the axis 18 in the radial direction 28. As shown with reference to FIGS. 1 and 3, the nanoparticles 36 are disclosed as being located on the portions of the base layer 30 shown in cross-section. The nanoparticles 36 are not shown as being present between the cross-section portions 30 of the base layer in the radial direction 28 simply for sake of clarity. They may or may not be located on the portions of the inner surface 42 of the base layer 30 that are not cross-sectioned.

The provision of self-assembled, aggregated high aspect ratio metallic nanoparticles 36 may provide better enhancement of the SERS process. The nanoparticles 36 may support plasmonic resonances that may be required for the SERS effect. The nanoparticles 36 may increase enhancement factors of the measurement, and may allow for single-molecule SERS for molecules at junctions between aggregated nanoparticles 36. This may result due to localized surface plasmon coupling between nanoparticles 36 and an enhanced electromagnetic field intensity localized at nanoparticle 36 junctions. Further, if the resonance between the incident radiation and the electronic absorption maxima overlap, greater SERS enhancements for these nanoparticles 36 are projected to occur.

Figure 5:
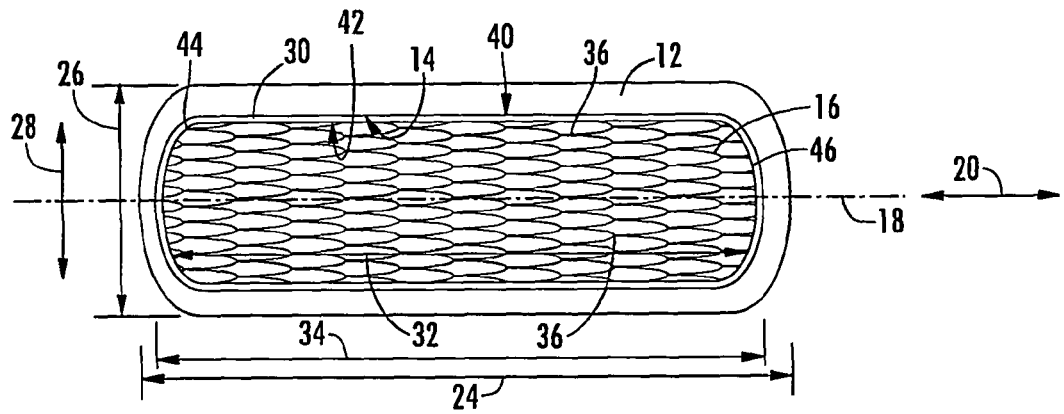
FIG. 5 is a cross-sectional view of a capillary/waveguide in accordance with another exemplary embodiment.

With reference to FIG. 5, the nanoparticle array 36 is assembled along the entire inner surface 42 of the base layer 30 and the nanoparticles 36 are in the form of rods. The rods are arranged so that they extend in the axial direction 20 and are located next to one another so as to prevent the inner surface 42 from being viewed within the cavity 16. However, other arrangements are possible in which portions of the inner surface 42 may be viewed due to gaps being present between adjacent nanoparticles 36.

Two purposes may be served through the use of high aspect ratio nanoparticles 36 such as rods or wires. First, the optical properties of the nanoparticles 36 are tunable through control of the morphology, allowing matching of the optical frequencies to the excitation and Raman scattering frequencies. Second, the anisotropic structures support self-assembled deposition on the inner surface 42. Locally intense enhancements on the order of $10^{12}$ may be observed at the interfaces between these types of nanoparticles 36. The self-assembly allows the possibility of a high density of highly active SERS sites. Self-assembly can be carried out in solution phase. However, it is to be understood that other forms of self-assembly can be used such as vapor deposition or lithography in other exemplary embodiments. The use of self-assembly through a solution allows for the ability to modify the inner surface of the capillary/waveguide 74, and may promote reproducibility when making multiple flow cells 10.

With reference back to the flow cell 10 of FIG. 1, a Raman imaging probe may be used to obtain characteristics of the analyte 22 for identification. However, it is to be understood that other devices, such as optical filters and photomultipliers, may be used in the flow cell 10 for identification of the composition of the analyte 22. The Raman imaging probe may include a first laser 48 and a first sensor 50 that are each located on one side of a first micro-lens 52. The first sensor 50 may be in communication with a central processing unit, storage device, or other instrument by way of a cable 76. Information obtained from the first sensor 50 can be transported via the cable 76. The first laser 48 may likewise be in communication with a central processing unit or other device by way of the cable 76 so that such device can instruct the first laser 48 to generate excitation light 38. The first micro-lens 52 may be present in order to focus the excitation light 38 generated by the first laser 48 into the capillary/waveguide 74. The first micro-lens 52 may be coated in order to block Raman scattering from the sensor 50. The first laser 48 and first sensor 50 may be located on one side of the first micro-lens 52 in the axial direction 20 while the capillary/waveguide 74 is located on the opposite side of the first micro-lens 52 in the axial direction.

The excitation light 38 enters the capillary/waveguide 74 through the inlet 44 and travels in the axial direction 20 through the cavity 16. The Raman signal is collected in the backscattering mode such that the first sensor 50 is arranged 180° from the direction of travel of the excitation light 38 in the axial direction 20. This arrangement may ensure that the field of view of the first sensor 50 overlaps with the excitation volume. The first sensor 50 collects light scattering arising from the SERS effect. As the first sensor 50 collects data, the analyte 22 may flow constantly through the capillary/waveguide 74 by entering the inlet 44 of cavity 16 and traversing therethrough before exiting at the outlet 46. Such an arrangement may avoid long wait times that may occur in instances in which the analyte 22 is exchanged into and out of a sealed or non-flowing capillary/waveguide 74. The excitation light 38 is applied in the axial direction 20 through the capillary/waveguide 74 which is a waveguiding approach to maximize interaction with the interior surface of the capillary/waveguide 74 that includes the nanoparticles 36 and possibly the base layer 30. The excitation light 38 may hit the entire surface formed by the nanoparticles 36 and/or the inner surface 42 and such light can scatter and bounce back to the first sensor 50. The surface formed by the nanoparticles 36 and/or the inner surface 42 can be a reflective surface.

The waveguiding approach may be distinguished from SERS techniques in which the laser light is directed through the side wall of the capillary/waveguide 74 (in the radial direction 28) instead of in the axial direction 20. However, certain exemplary embodiments exist in which the laser light is directed in the radial direction 28 instead of or in addition to the axial direction 20.

The use of a narrow reflective capillary/waveguide 74 may be a way to enhance the classical Raman measurement by a factor from 12 to 30 for nonabsorbing analytes 22 such as $CO_2$ and $CH_4$ as compared to regular Raman probes. These gains may be realized from the increased interaction length of the excitation light 38 with the sample, and from an improved collection efficiency of the scattered light. Fiber optics may assist in implementing this particular approach. Interaction along the entire axial length of the excitation section 32 may occur with the excitation light 38. As such, it may be the case that excitation light 38 directed to a single point is not present in certain exemplary embodiments. The surface formed by the base layer 30, and possibly the nanoparticles 36 and/or combination of base layer 30 and nanoparticles, may be reflective such that incident excitation light 38 is recycled along the entire axial length 24 of the capillary/waveguide 74. The width or cross-section of the excitation light 38, whether due to the cross-section of the first laser 48 and/or the first micro-lens 52, may be greater than, the same as, or lesser than the diameter or cross-section of the cavity formed by the nanoparticles 36 and/or the inner surface 42.

The capillary/waveguide 74, first laser 48, first sensor 50, and other components may be held by a spring-loaded chuck 60. Cavities within the spring-loaded chuck 60 may define the passageways 70 and 72, and may define or receive the inlet and outlet ports 66, 68. The spring-loaded chuck 60 may be adjustable so that it can move in various directions to allow the capillary/waveguide 74 to thus be positioned in various locations. In this regard, only the capillary/waveguide 74 may be adjustably positioned, or additional components of the flow cell 10 such as the passageways 70, 72 and the ports 66, 68 may also be positionable. The spring-loaded chuck 60 can be moved in the axial direction 20 and may be capable of being rotated about the axis 18 360°. Further, the spring-loaded chuck 60 may be adjustable in a second direction 62 that is perpendicular to the axial direction 20 and is essentially the same as the radial direction 28 with reference to FIG. 1. Still further, the spring-loaded chuck 60 may be adjustable in a third direction 64 that is perpendicular to both the axial direction 20 and the second direction 62. The third direction 64 extends into the page of the drawing of FIG. 1. As such, with reference to FIG. 1 by setting a reference frame of the inlet 44 as vertically higher and the outlet 46 as vertically lower, the spring-loaded chuck 60 may be adjustable so as to be capable of moving up and down, left and right, and into and out of the page, in addition to being rotatable.

The aforementioned adjustability allows various components of the flow cell 10 to be adjusted in the directions previously mentioned. This arrangement may allow for reproducible positioning and adjustment of the capillary/waveguide 74. The spring-loaded chuck 60 may be mounted onto a four-dimensional stage to allow for the three linear adjustments in addition to the rotational adjustment.

The flow cell 10 may also include a backup Raman imaging probe that can be used in case the primary Raman imaging probe fails. The backup Raman imaging probe has a second laser 54 and a second sensor 56. A second micro-lens 58 may also be present. The second laser 54 and second sensor 56 may be located on one side of the second micro-lens 58 in the axial direction 20 while the capillary/waveguide 74 is located on the opposite side of the second micro-lens 58 in the axial direction 20. A cable 78 may be in communication with the second sensor 56 in order to transport data obtained by the second sensor 56 to a central processing unit or other device. The second laser 54 may be in communication with the central processing unit or other device via the cable 78 in order to receive instructions as to when to emit excitation light. The second laser 54 may generate excitation light that is focused by the micro-lens 58 so that this excitation light is directed in the axial direction 20 into the outlet 46 and through the cavity 16 in the axial direction 20 and out of the inlet 44. The cables 76 and 78 may be either electrical cables, fiber optic cables, or variously arranged in accordance with different embodiments.

The second laser 54, second sensor 56, and second micro-lens 58 may be provided and arranged as those previously discussed with respect to the first laser 48, first sensor 56, and first micro-lens 58 and a repeat of this information is not necessary. The presence of the second Raman imaging probe may be provided as a back-up to the first in case the first Raman imaging probe fails to function.

Figure 14:
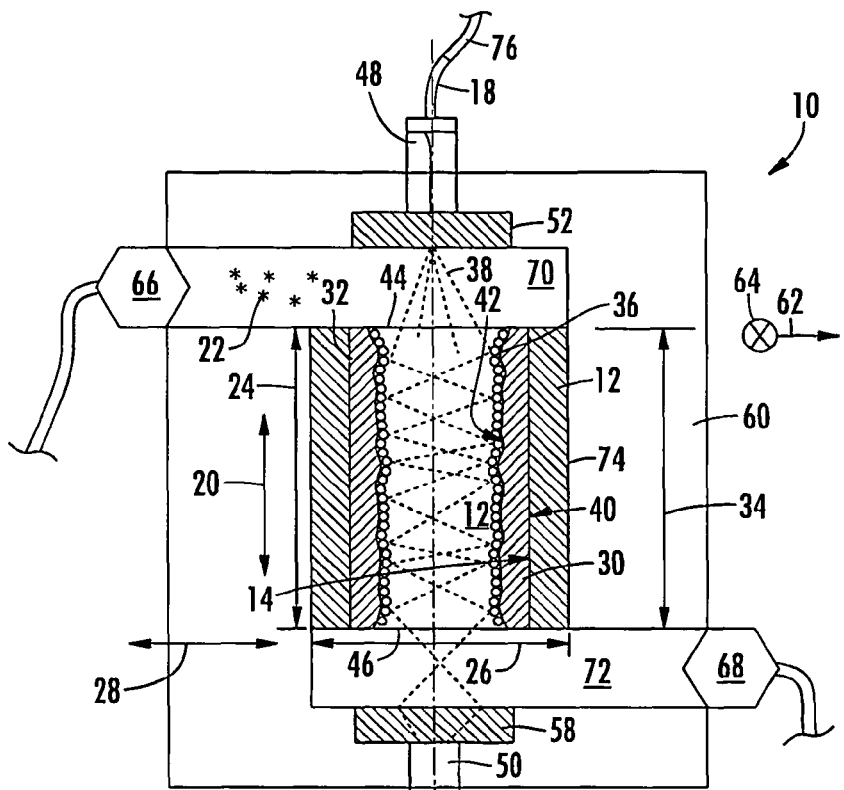
FIG. 14 is a partial cross-sectional view of a waveguide and flow cell in accordance with a different exemplary embodiment.

FIG. 14 discloses another exemplary embodiment of the waveguide 74. The waveguide 74 is incorporated into a flow cell 10 and includes basic structure similar to that previously disclosed, and a repeat of this information is not necessary. The waveguide 74 of FIG. 14 differs from that of previous embodiments in that the laser 48 and sensor 50 are located on opposite sides of the base structure 12, base layer 30, and nanoparticles 36 in the axial direction 20. The laser 48 generates excitation light 38 through the first micro-lens 52 and into the cavity 16 as previously disclosed. The excitation light 38 enters the inlet 44 and travels in the axial direction 20 and exits the outlet 46 where it moves through the second micro-lens 58. The second micro-lens 58 is located between the outlet 46 and the sensor 50 in the axial direction 20 and the sensor 50 collects the Raman scattering for analysis. The other components of the flow cell 10 and waveguide 74 can be the same as those previously described and a repeat of this information is not necessary.

Figure 15B:
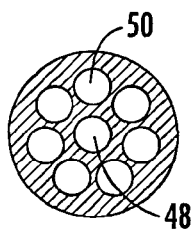
FIG. 15B is a cross-sectional view taken along line 15B-15B of FIG. 15A.
Figure 15A:
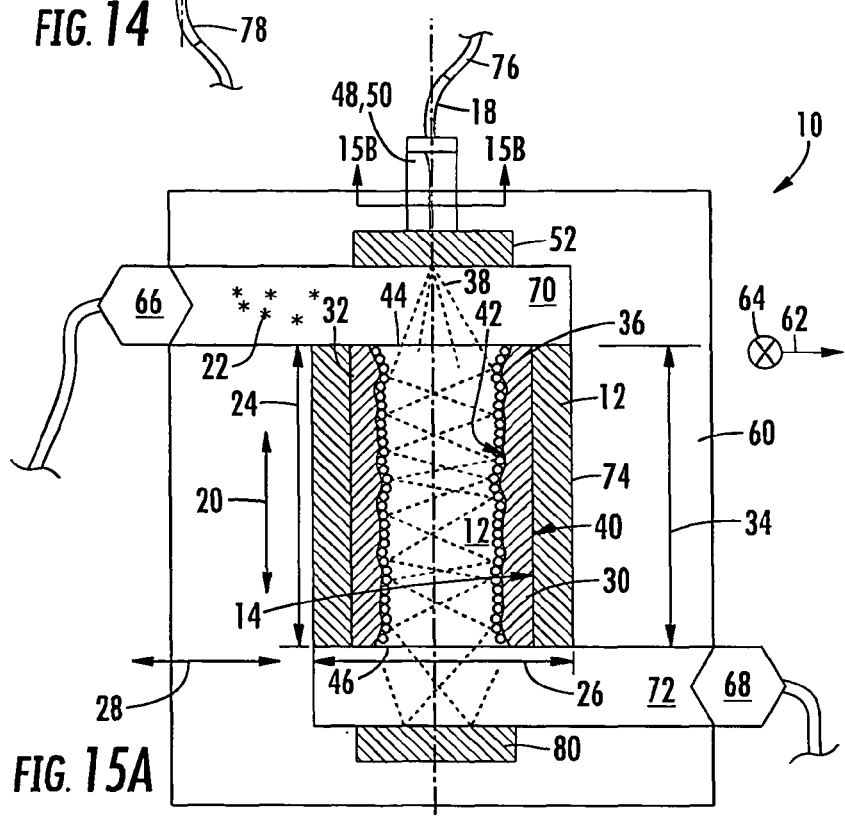
FIG. 15A is a partial cross-sectional view of a waveguide and flow cell in accordance with yet another exemplary embodiment.

An additional exemplary embodiment of the waveguide 74 incorporated into a flow cell 10 is shown with reference to FIG. 15A. Here, the laser 48 and sensor 50 are both located on one side of the first micro-lens 52 in the axial direction 20. The first micro-lens 52 is thus located so that it is between the laser 48, sensor 50 on one side, and the base structure 12, base layer 30, and nanoparticles 36 on the opposite side in the axial direction 20. The laser 48 generates excitation light 38 that travels in the axial direction 20 through the cavity 16. The excitation light 38 creates Raman scattering and exits the outlet 46 and goes through the passageway 72. A mirror 80 is located beyond the passageway 72, or defines part of the passageway 72, in the axial direction 20. The excitation light 38 is reflected off of mirror 80 and reenters the cavity 16 through the outlet 46. The excitation light 72 may travel back in the axial direction 20 through the first micro-lens 52 and be collected by the sensor 50.

With reference now to FIG. 15B, the arrangement of the laser 48 and sensor 50 is shown. The laser 48 may be located in the radial center of the device, and the sensor 50 with multiple collection portions can encircle the centrally located laser 48. In other arrangements, a single collection portion can be associated with the sensor 50. The cable 76 may be a fiber optic cable that is capable of transporting information received by sensor 50 and transporting instructions to the laser 48 to instruct same to generate excitation light 38.

The nanoparticles 36 may be made of gold or silver in accordance with certain exemplary embodiments. In yet other arrangements, some of the nanoparticles 36 may be made of gold while the rest are made of silver. Also, the nanoparticles 36 may be made of both gold and silver in that a shell of gold can be located around a core silver particle, or vice versa. Also, the nanoparticles 36 may be coated with a thin protective layer, such as silica. In accordance with one exemplary embodiment, all of the nanoparticles 36 are made of gold and the base layer 30 is a thin layer of bulk gold that is bonded to the inner surface 14 of the base structure 12. The capillary/waveguide 74 can be assembled such that the base layer 30 is first bonded onto the inner surface 14, and subsequently the nanoparticles 36 are self-assembled onto the inner surface 42 of the base layer 30. Gold layers 30 and nanoparticles 36 may be more stable than silver layers 30 and nanoparticles 36, however it is the case that silver layers 30 and nanoparticles 36 are used in other arrangements. The gold layer 30 and nanoparticles 36 may better resist chemical attack and oxidation and may be more likely to retain their optical properties with repeated use. The base layer 30 may be made of a thickness sufficient to convert the base structure 12 into a waveguide. Attachment of gold nanoparticles 36 and the gold base layer 30 may be accomplished through thiol linkages.

Figure 11:
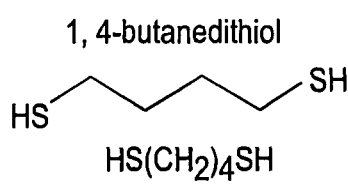
FIGS. 11-13 are examples of different linker molecules that may be used to attach nanoparticles to the base layer in accordance with different exemplary embodiments.
Figure 12:
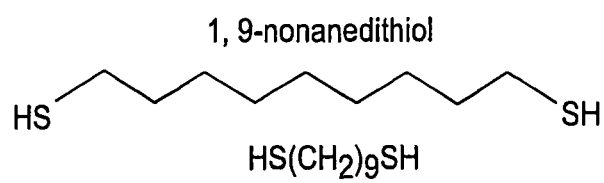
Figure 13:
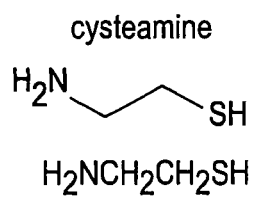

With reference now to FIGS. 11-13, various thiols are disclosed that can be used in accordance with different exemplary embodiments. The thiols in FIGS. 11-13 are examples of linker molecules that can be used to attach nanoparticles 36 to a base layer 30 made of silver. In general, dithiols are straight-chain alkanes (hydrocarbons) with sulfur containing thiol groups on each end. The two examples shown in FIGS. 11 and 12 indicate variability in the length of the hydrocarbon chain that may be considered when examining attachment chemistry. Aminothiols are similar molecules, though with one thiol group and one amino group, in which the HS is replaced with $H_2N$ as shown in FIG. 13. Thiol groups may be used when attaching to a gold surface due to the strength of the Au—S bond. Amino groups may be used for attachment to silver surfaces.

The capillary/waveguide 74 may be constructed by first providing a base structure 12 and then subsequently coating the inner surface 14 of the base structure 12 with a base layer 30 to provide the waveguide effect. After this step, the nanoparticle array 36 may be attached to the base layer 30 to add the SERS-generating element. The nanoparticle array 36 may be coated with a bonding element such as thiol groups or amino groups first before the attachment step. The capillary/waveguide 74 may be characterized with high magnification techniques, and a Raman signal generated within the capillary/waveguide 74 may be measured.

Figure 16:
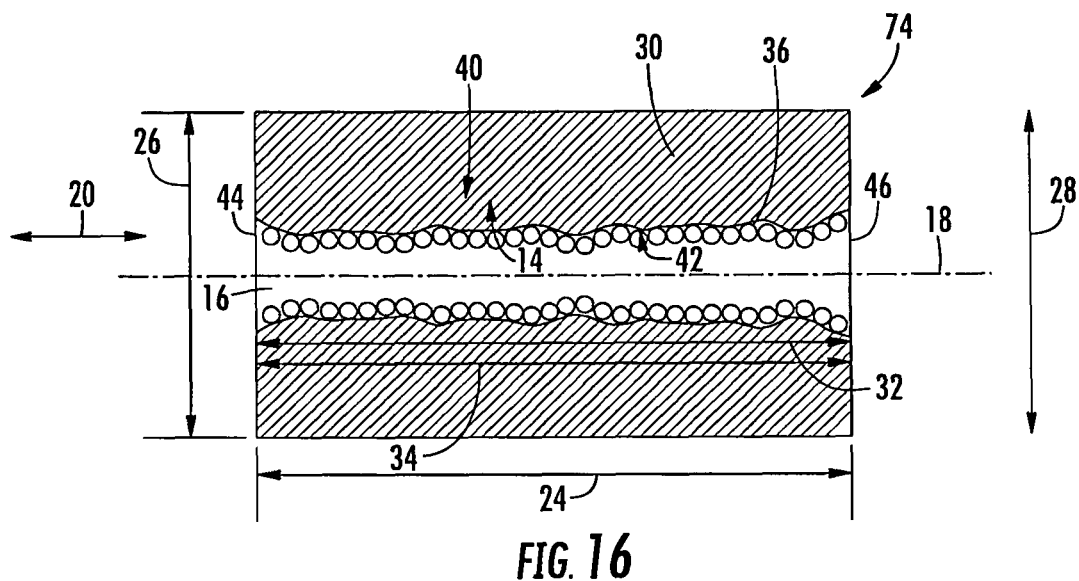
FIG. 16 is a cross-sectional view of a capillary/waveguide in accordance with a different exemplary embodiment.

FIG. 16 discloses another exemplary embodiment of the capillary/waveguide 74. Here, a base structure 12 is not present. Instead, base layer 30 may be made slightly larger in the radial direction 28. The nanoparticles 36 can be carried by the base layer 30 in manners previously discussed. The capillary/waveguide 74 may thus be a tube made of solid gold or silver in some embodiments with the nanoparticles 36 attached to the inner surface 42. However, such a design may be cost probative in that a solid gold or silver tube constituting the base layer 30 must be provided.

The flow cell 10 can be constructed so that it is a compact, rugged device capable of taking measurements of the analyte 22 outside of an optical laboratory environment. The flow cell 10 may be used in flue stack monitoring, glove boxes, confined spaces, or as a detector for analytical instrumentation such as the identification of effluents from a gas chromatography column. The flow cell 10 may function with standard optical fibers and sample delivery systems. Further, the flow cell may allow for reproducible capillary/waveguide 74 positioning, simple capillary/waveguide 74 exchange, and capillary/waveguide 74 protection by its housing within the spring-loaded chuck 60. The flow cell 10 may employ small fans and miniature diode lasers 50, 54 and if combined with handheld Raman instruments may be field-portable or a standalone monitor. The flow cell 10 may provide for an improvement of up to 200 times the detection limits of Raman spectroscopy. Although described as having both excitation light 38 directed in the axial direction 20, and nanoparticles 36 on the inner surface 42, only one or none of these features may be present in other exemplary embodiments. Further, although described as being used for analytes 22 that are gasses, it is to be understood that the flow cell 10 may be used to evaluate analytes 22 that are liquids as well.

Further, it is to be understood that the terms "waveguide" and "capillary/waveguide" as used herein are interchangeable and encompass one another. These two terms are used simply for sake of convenience and it is to be understood that they are each broad enough to encompass the other and in effect carry the same meaning.

Experiments Carried Out in Accordance with Certain Exemplary Embodiments

Figure 6:
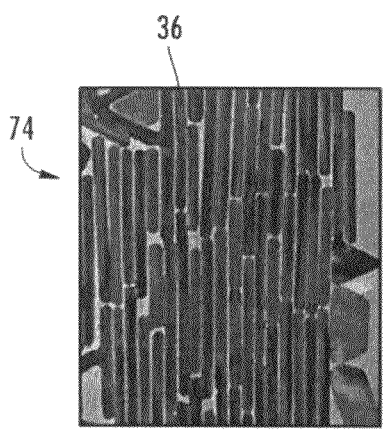
FIG. 6 is a scanning electron microscopy image of high-aspect nanorods of a capillary/waveguide in accordance with one exemplary embodiment.
Figure 7:
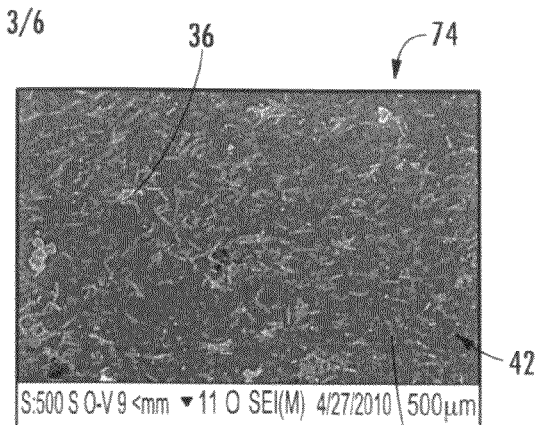
FIG. 7 is a scanning electron microscopy image of dilute nanorod deposition inside of a gold coated capillary/waveguide in accordance with one exemplary embodiment.

In accordance with an experiment carried out with respect to the flow cell 10, a thin gold surface making up the base layer 30 was provided on the base structure 12. The nanoparticle array 36 was made of a series of high-aspect nanorods. FIGS. 6 and 7 illustrate this experiment. The nanorods have an aspect ratio of approximately 12:1 and are approximately 300 nm×25 nm. The nanorods have an optical resonance associated with the shorter dimension that matches a 532 nm excitation wavelength. The nanoparticle array 36 was formed on the base layer 30 by a dilute nanorod solution which resulted in incomplete surface coverage of the inner surface 42 and minimal self-assembly.

Additional experiments were carried out in accordance with different embodiments. First, an experiment was conducted on capillary/waveguides 74 that included base layers 30 made of silver, but with no nanoparticles 36 present. All of the capillary/waveguides 74 were of 2 mm in diameter. Nitrogen in air was characterized at 532 nm/100 mW excitation light 38 with a 60 second collection time. Capillary/waveguides 74 of different axial lengths 24 were examined. It was found that as the axial lengths 24 of the capillary/waveguides 74 were increased, the intensity of the Raman scattering was likewise increased.

Another experiment using the same conditions as in the immediately preceding paragraph was conducted on various capillary/waveguide 74 axial lengths 24 to identify nitrogen and oxygen in air. The intensity of nitrogen and oxygen was plotted against capillary/waveguide 74 axial length 24 and it was determined that a maximal signal was observed between 25-50 centimeters of axial length 24.

An additional experiment was conducted to determine the effect of capillary/waveguide 74 diameter on the enhancement factor of the Raman process. A capillary/waveguide 74 was provided that had a base layer 30 of silver. The axial length 24 used was 25 centimeters, and the capillary/waveguides 74 did not have nanoparticles 36. Nitrogen in air was characterized and compared to a Raman nitrogen signal that was generated without the use of a capillary/waveguide 74 which is defined as the baseline. For a nominal 1.0 millimeter diameter capillary/waveguide 74 the enhancement factor over the baseline was approximately 4.5, for a nominal 2.0 millimeter diameter capillary/waveguide 74 the enhancement factor over the baseline was approximately 15, and for a nominal 3.2 millimeter diameter capillary/waveguide 74 the enhancement factor over the baseline was approximately 25.

Figure 8:
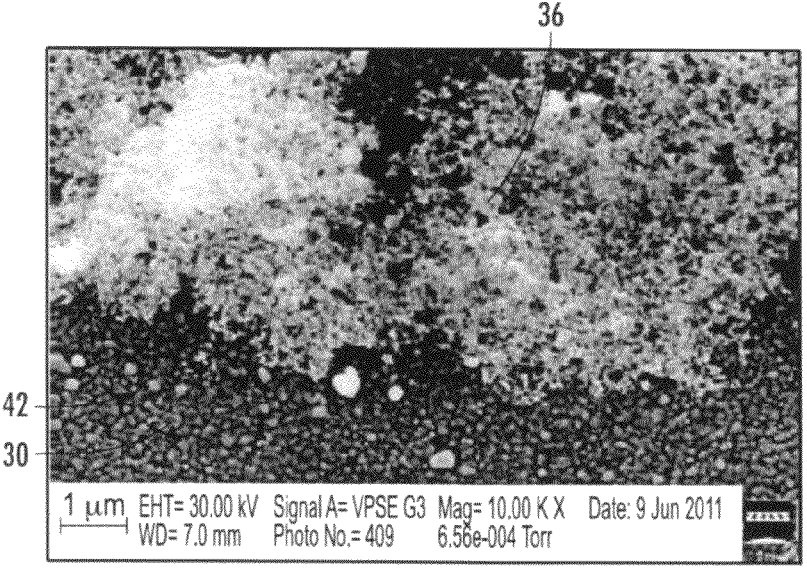
FIGS. 8 and 9 are scanning electron microscopy images of nanoparticles located on a base layer in accordance with another exemplary embodiment.
Figure 9:
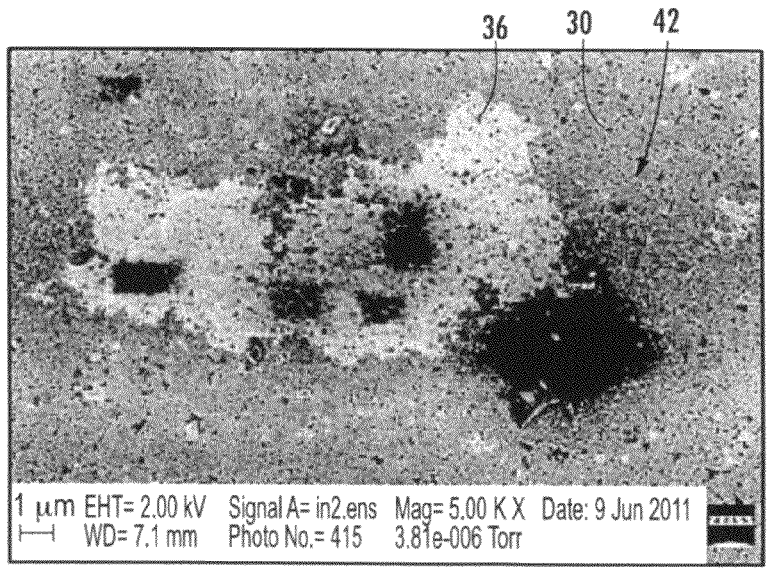

A still further experiment conducted in accordance with an additional exemplary embodiment is shown with reference to FIGS. 8 and 9. These figures are scanning electron microscopy images of nanoparticles 36 that are gold nanorods having a size of approximately 25 micrometers×60 micrometers. The nanoparticles 36 are deposited onto an inner surface 42 of a base layer 30 that is made of silver. The nanoparticles 36 are shown as having a filigree-like structure in the figures. The darker, more pebble-like structures are formerly colloidal silver particles that were deposited out of solution onto the inner surface 14. The nanoparticles 36 were coated with dithiol linker molecules. As shown, the nanoparticles 36 do not completely cover the inner surface 42 but instead leave various portions of the inner surface 42 uncovered.

Figure 10:
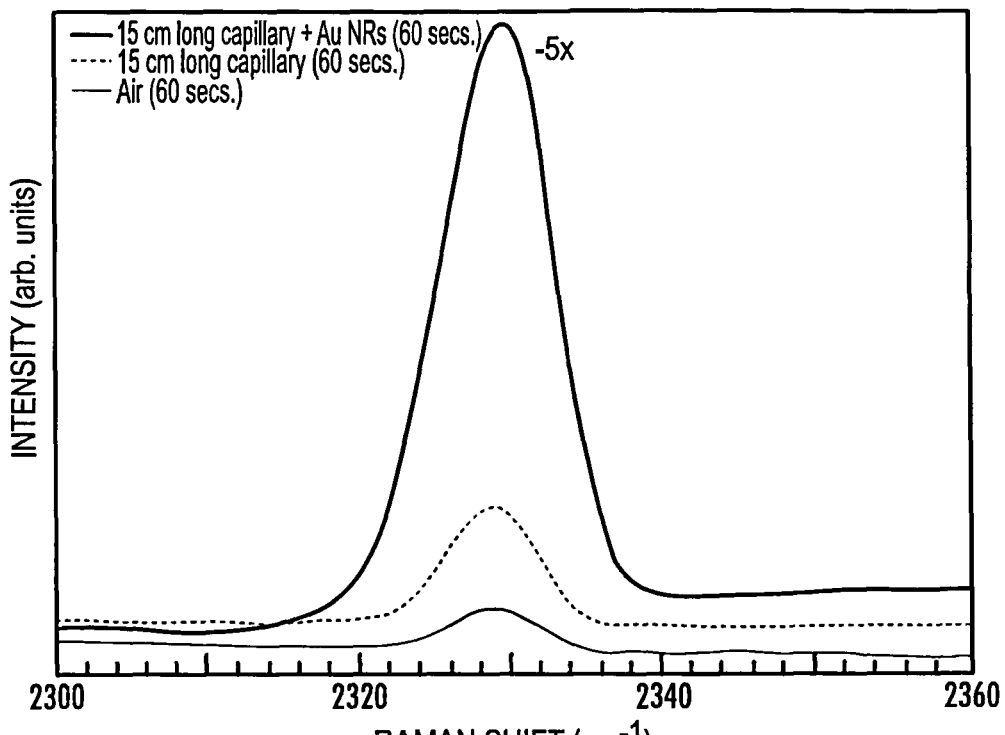
FIG. 10 is a plot of intensity versus Raman shift for three different samples in accordance with another exemplary embodiment.

With reference now to FIG. 10, a plot of intensity versus Raman shift was created for nitrogen from air for three different samples. The bottom plot was obtained through Raman measurements with no capillary/waveguide 74 present. The middle plot was made from a capillary/waveguide 74 having a silver base layer 30 but without the presence of microparticles 36. The top plot was made with a capillary/waveguide 74 having a silver base layer 30 with gold 25 micrometer×60 micrometer nanoparticles 36. All other experimental parameters for the three samples such as laser wavelength and power, detection time, and collection optics were kept the same. A signal enhancement of approximately 5 times was seen for the capillary/waveguide 74 that included the nanoparticles 36 as opposed to the capillary/waveguide 74 that did not have the nanoparticles 36 but instead had only a silver base layer 30.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. A waveguide for use with surface-enhanced Raman spectroscopy, comprising: a base structure having an inner surface that defines a through cavity through the base structure, wherein the inner surface extends about an axis such that the through cavity extends in an axial direction, wherein an analyte is capable of being transferred via the through cavity, wherein the base structure has an axial length that is longer than a radial length of the base structure;
a base layer located on the inner surface of the base structure, wherein the base layer extends in the axial direction along an axial length of an excitation section;
nanoparticles bonded to the base layer;
a first micro-lens that directs an excitation light generated by a laser into the through cavity;
a second micro-lens, for receiving the excitation light and transmitting the light to a data collection sensor;
wherein when the excitation light is directed into the through cavity of the base structure by the first micro-lens a plurality of molecules of the analyte are present within the through cavity and the second micro-lens receives the light from the through cavity and directs it to the sensor and wherein the laser and the first micro lens are located on one side of the base structure and the second micro-lens and the sensor are located on an opposite side of the base structure.

2. The waveguide as set forth in claim 1, wherein the base structure is a tube, and wherein the excitation section extends along the entire axial length of the base structure.

3. The waveguide as set forth in claim 2, wherein the nanoparticles are distributed along the entire axial length of the excitation section and are uniformly distributed along the entire axial length of the excitation section.

4. The waveguide as set forth in claim 3, wherein the base layer has an outer surface that is contiguous with the inner surface of the base structure, and wherein the base layer has an inner surface that is contiguous with the nanoparticles.

5. The waveguide as set forth in claim 4, wherein the base layer and the nanoparticles are comprised from the group consisting of silver, gold, and combinations thereof, wherein the analyte is transferred into an inlet of the through cavity and out of an outlet of the through cavity, wherein the excitation light is transferred into the inlet of the through cavity, wherein the analyte is a fluid.

6. The waveguide as set forth in claim 5, further comprising a flow cell that houses the waveguide and allows introduction of the analyte that is a gas stream and the excitation light.

7. The waveguide as set forth in claim 1, wherein the excitation light is generated by a first laser, wherein a plurality of molecules of the analyte are present within the through cavity when the excitation light is directed into the through cavity; and further comprising:
a first micro-lens that focuses the excitation light into the through cavity;
a mirror that reflects excitation light back towards the sensor;
wherein the first laser, the sensor and the first micro-lens are located on one side of the base structure, the base layer, and the nanoparticles in the axial direction and wherein the mirror is located on an opposite side of the base structure, the base layer, and the nanoparticles in the axial direction.

8. A waveguide for use with surface-enhanced Raman spectroscopy, comprising:
a base structure having an inner surface that defines a through cavity through the base structure, wherein the inner surface extends about an axis such that the through cavity extends in an axial direction, wherein an analyte is capable of being transferred via the through cavity, wherein the base structure has an axial length that is longer than a radial length of the base structure;
a base layer located on the inner surface of the base structure, wherein the base layer extends in the axial direction along an axial length of an excitation section;
nanoparticles carried by the base layer;
excitation light directed into the through cavity of the base structure such, that the excitation light extends in the axial direction through the through cavity along the entire axial length of the excitation section a sensor that collects data upon direction of the excitation light through the through cavity of the base structure, wherein the sensor is a Raman spectrometer;
wherein the excitation light is generated by a first laser, wherein a plurality of molecules of the analyte are present within the through cavity when the excitation light is directed into the through cavity; and further comprising; a first micro-lens that focuses the excitation light into the through cavity; a second micro-lens that receives light from the through cavity for transmission to the sensor; wherein the first laser and the first micro-lens are located on one side of the base structure, the base layer, and the nanoparticles in the axial direction and wherein the second micro-lens and the sensor are located on an opposite side of the base structure, the base layer, and the nanoparticles in the axial direction.

9. The waveguide as set forth in claim 8, further comprising:
   a second laser that is part of a backup system that generates second excitation light into the through cavity, wherein the second laser is located on an opposite side of the base structure than the first laser in the axial direction;
   a second sensor that is part of a backup system that is a Raman spectrometer that collects data upon direction of the second excitation light through the through cavity of the base structure;
   the second micro-lens that is part of a back up system that focuses the second excitation light into the through cavity, wherein the second laser and the second sensor are located on one side of the second micro-lens and wherein the base structure, the base layer and the nanoparticles are located on an opposite side of the micro-lens; and
   a spring loaded chuck that engages the base structure, wherein the spring loaded chuck is capable of being linearly adjusted in three directions such that the base structure is capable of being linearly adjusted in the axial direction and in two directions perpendicular to the axial direction and perpendicular to one another, and wherein the spring loaded chuck is capable of being rotationally adjusted such that the base structure is capable of being rotated about the axis.

10. A waveguide for use with surface-enhanced Raman spectroscopy, comprising:
    a base structure that is a tube that has an inner surface that defines a cavity, wherein the base structure has an axis located in the cavity and that extends in an axial direction, wherein multiple molecules of an analyte are capable of being located within the cavity at the same time;
    a base layer located on the inner surface of the base structure, wherein the base layer extends in the axial direction along an axial length of an excitation section; and
    nanoparticles carried by the base layer, wherein the nanoparticles are uniformly distributed along the entire axial length of the excitation section wherein multiple molecules of the analyte are present within the cavity when the excitation light is directed into the cavity, and further comprising a micro-lens that focuses the excitation light into the cavity, wherein the laser that generates the excitation light and the sensor are located on one side of the micro-lens and wherein the base structure, the base layer and the nanoparticles are located on an opposite side of the micro-lens; and
    wherein the excitation section extends along the entire axial length of the base structure, wherein the nanoparticles are disposed along the entire axial length of the excitation section, wherein the base layer has an outer surface that is contiguous with the inner surface of the base structure, and wherein the base layer has an inner surface that is contiguous with the nanoparticles; and further comprising a spring loaded chuck that engages the base structure, wherein the spring loaded chuck is capable of being linearly adjusted in three directions such that the base structure is capable of being linearly adjusted in the axial direction and in two directions perpendicular to the axial direction and perpendicular to one another, and wherein the spring loaded chuck is capable of being rotationally adjusted such that the base structure is capable of being rotated about the axis, in combination with the rest of the limitations of the claim.

11. The waveguide as set forth in claim 10, wherein the base structure has an axial length that is longer than a radial length of the base structure, wherein the radial length of the base structure is an outer diameter of the base structure.

12. The waveguide as set forth in claim 10, further comprising:
    a laser that generates excitation light, wherein the excitation light is directed into the cavity such that the excitation light extends in the axial direction along the entire axial length of the excitation section; and
    a sensor that is a Raman spectrometer that collects light scattering created by a surface-enhanced Raman spectroscopy effect brought about by the excitation light and directed along the axial length of the waveguide.

13. The flow cell as set forth in claim 10, wherein a plurality of molecules of the analyte are present within the through cavity when the excitation light is directed into the through cavity, wherein the laser is located on one side of the base structure, the base layer, and the nanoparticles in the axial direction and wherein the sensor is located on an opposite side of the base structure, the base layer, and the nanoparticles in the axial direction.

14. The flow cell as set forth in claim 10, wherein the base structure is made of glass, wherein the base layer and the nanoparticles are made of gold, wherein the analyte is transferred into an inlet of the cavity and out of an outlet of the cavity, wherein the excitation light is transferred into the inlet of the cavity, wherein the analyte is a gas, wherein the nanoparticles form an inner surface that is a reflective surface that functions to reflect laser light.

15. A method of operating a wave guide, comprising the steps of:
    providing a base structure having an inner surface that defines a cavity, wherein the inner surface extends about an axis such that the cavity extends in an axial direction, wherein the base structure has an axis and wherein the axis is located in the cavity;
    providing a first micro-lens that directs an excitation light generated by a laser into the through cavity;
    providing a second micro-lens, for receiving the excitation light and transmitting the light to a data collection sensor;
    applying a base layer to the inner surface of the base structure, wherein the base layer extends in the axial direction along an axial length of an excitation section; and
    bonding nanoparticles onto the base layer such that the nanoparticles are uniformly distributed along the entire axial length of the excitation section;
    wherein when the excitation light is directed into the through cavity of the base structure by the first micro-lens a plurality of molecules of the analyte are present within the through cavity and the second micro-lens receives the light from the through cavity and directs it to the sensor and wherein the laser and the first micro lens are located on one side of the base structure and the second micro-lens and the sensor are located on an opposite side of the base structure.

16. The method as set forth in claim 15, wherein the base structure is made of glass, and wherein the base layer is selected from the group consisting of gold and silver, and wherein the nanoparticles are selected from the group consisting of gold and silver.

17. The method as set forth in claim 15, wherein the base structure is a tube and wherein the base layer is applied to the entire inner surface of the tube such that the excitation section extends along the entire axial length of the inner surface of the tube, wherein the bonding nanoparticles step is accomplished through solution deposition such that the nanoparticles are applied along an entire axial length of an inner surface of the base layer and 360° about the axis in a radial direction on the inner surface of the base layer.

18. The method as set forth in claim 15, wherein the bonding the base layer step is accomplished through solution deposition.

19. The method as set forth in claim 15, wherein the base structure, the base layer, and the nanoparticle assembly is used in a surface-enhanced Raman spectroscopy process.

* * * * *